United States Patent [19]

Ovadia et al.

[11] Patent Number: 4,898,942
[45] Date of Patent: Feb. 6, 1990

[54] PROCESS FOR MANUFACTURING DIAZINON

[75] Inventors: David Ovadia, Omer; Ernestine Mandler, Beer-Sheva, both of Israel

[73] Assignee: Makhteshim Chemical Works, Ltd., Beer Sheva, Israel

[21] Appl. No.: 239,341

[22] Filed: Aug. 30, 1988

Related U.S. Application Data

[63] Continuation of Ser. No. 917,195, Oct. 19, 1986, abandoned.

[30] Foreign Application Priority Data

Oct. 14, 1985 [IL] Israel ......................................... 76705

[51] Int. Cl.$^4$ ................................................. C07F 9/65
[52] U.S. Cl. ..................................................... 544/243
[58] Field of Search ......................................... 544/243

[56] References Cited

U.S. PATENT DOCUMENTS

| | | | |
|---|---|---|---|
| 3,107,245 | 10/1963 | Gaunt et al. | 544/243 |
| 3,107,246 | 10/1963 | Ferguson | 544/243 |
| 3,205,231 | 9/1965 | Fest | 544/243 |
| 3,367,935 | 2/1968 | Curry et al. | 544/243 |
| 3,432,503 | 3/1969 | Ferguson . | |
| 3,792,132 | 2/1974 | Bernhart | 558/100 |
| 4,066,642 | 1/1978 | Sury et al. | 544/243 |
| 4,323,678 | 4/1982 | Schilling | 544/243 |
| 4,326,059 | 4/1982 | Gargano et al. | 544/243 |

FOREIGN PATENT DOCUMENTS

| | | | |
|---|---|---|---|
| 0623700 | 7/1961 | Canada | 546/25 |
| 0122255 | 9/1979 | Japan | 558/100 |

Primary Examiner—Mukund J. Shah
Assistant Examiner—Diana G. Rivers
Attorney, Agent, or Firm—Browdy & Neimark

[57] ABSTRACT

An improved process for the production of Diazinon substantially free of toxic by-products in high yield and very high purity which involves mixing 2-isopropyl-4-methyl-6-hydroxypyrimidine with solid sodium or potassium hydroxide in a ketone or ether solvent at a temperature of about 50°–60° C. until a homogeneous mixture is formed, adding diethylthiophosphoryl chloride to the homogeneous mixture, keeping the mixture at a temperature of 55°–80° C. until the reaction is complete, and separating the Diazinon formed.

11 Claims, No Drawings

4,898,942

PROCESS FOR MANUFACTURING DIAZINON

This application is a continuation of application Ser. No. 917,195, filed Oct. 9, 1986, now abandoned.

BACKGROUND OF THE INVENTION

The present invention concerns the improved process for preparing diazinon which, owing to its good insecticidal and acaricidal properties, is of great commercial value for the destruction of insect pests.

Diazinon was produced for the first time by Glysin and Margot by reacting 2-isopropyl-4-methyl-6-hydroxypyrimidine (hereafter hydroxypyrimidine) with diethylthiophosphoryl chloride (hereinafter TPC) in an inert solvent, in the presence of potassium carbonate as described in United Kingdom Pat. No. 713,278.

In this heterogeneous reaction the potassium pyrimidinolate is initially formed by heating the hydroxypyrimidine with potassium carbonate in benzene, with simultaneous removal of the water formed. The potassium salt so produced is then reacted with TPC by heating for several hours, the potassium chloride formed extracted by washing with water, and the solvent removed under reduced pressure.

The standard process for the industrial manufacture of diazinon is carried out essentially by means of a 4-stage synthesis, wherein the above-mentioned heterogeneous reaction is the last stage. This last stage is usually carried out using a base such as sodium hydroxide in place of potassium carbonate.

Since 1952 several processes have been described in the literature, which modify this fourth(last) stage. Thus, U.S. Pat. No. 4,066,642 describes simultaneously reacting TPC and the hydroxypyrimidine in the presence of an acid acceptor such as sodium or potassium hydroxide while refluxing the inert solvent to remove the water as it it is formed without the use of any catalyst.

U.S. Pat. No. 4,326,059 describes the preparation of water-free sodium pyrimidinolate by refluxing sodium hydroxide with the hydroxypyrimidine in an aromatic solvent such as benzene in the presence of a phase transfer catalyst to remove any water by azetropic distillation and reacting the thus formed slurry with TPC.

Various other processes involving the use of a variety of catalysts to shorten the reaction times have been described. Suitable catalysts disclosed are mercury salts (U.S. Pat. No. 3,107,245), copper chloride (U.S. Pat. No. 3,107,246), copper nitrate (U.S. Pat. No. 3,367,935), and basic copper oxide (Japanese patent specification number 7,524,958).

In the processes which involve the use of catalysts, it was found that significant amounts of the highly toxic by-products, such as thiotepp (mono- or dithionotetraethylpyrophosphate), are formed. The presence of even small amounts of these by-products in diazinon is undesireable, from the point of view of operators or warm blooded animals that may come into contact therewith. Thus, U.S. Pat. No. 3,432,503 discloses a method of removing these by-products by refluxing the diazinon in an inert solvent in the presence of a base such as sodium hydroxide. However, this process not only requires a separate step subsequent to manufacture but also involves considerable loss of product during workup.

Recently U.S. Pat. No. 4,323,678 reported a one-pot reaction wherein β-isobutyrylaminocrotonic acid amide is cyclized in the presence of an alcohol, the resulting sodium pyrimidinolate precipitated by addition of a non-polar solvent, the alcohol/water removed by fractionation, and the sodium pyrimidinolate reacted with TPC at a temperature of 100° to 130° C.

However all of the above methods suffer from a variety of drawbacks. Examples are long reaction times, the need to use catalysts, the need for tricky manipulation of solvents, and/or the need for a separate step to remove toxic by-products. And none of these processes affords high yields of very pure diazinon.

OBJECTIVES OF THE INVENTION

It is an objective of the present invention to provide an improved method for preparing diazinon. It is a further objective of the present invention to provide a method more economical than known methods for the production of diazinon substantially free of toxic by-products in high yields and very high purity.

SUMMARY OF THE INVENTION

It has unexpectedly been discovered that diazinon can be prepared in an improved method by reacting the sodium or potassium salt of the hydroxypyrimidine with TPC in solution wherein the improvement comprises mixing the hydroxypyrimidine with solid sodium or potassium hydroxide in a ketone or ether solvent at a temperature of about 50°-60° C. until a homogeneous mixture is formed, adding TPC to this homogeneous mixture, keeping the mixture at a temperature of 55°-80° C. until the reaction is complete, and separating the diazinon formed.

By means of the present process commercially satisfactory reaction rates are achieved with yields of some 94 percent and purity better than 98 percent. This process is, thus, an improvement over the prior art in that a catalyst is not necessary; and the generally more difficult heterogeneous reaction can be avoided while affording a product in excellent yield containing essentially no toxic thiotepp as by-product.

DETAILED DESCRIPTION OF THE INVENTION

The process of the present invention requires the use of a ketone or ether solvent. Either fresh or recycled solvent may be of use, providing that the solvent is free from water. Examples of ketone solvents useful in the present invention are acetone, methyl ethyl ketone, methyl isobutyl ketone, methyl isopropyl ketone, and the like. Examples of ether solvents, useful in the present invention are dioxane, tetrahydrofuran, dibutyl ether, diisopropyl ether, dipropyl ether, butyl vinyl ether, butyl ethyl ether, dipentyl ether, isopentyl ether, dimethoxyethane bis-(2-methoxy ethyl) ether, and the like. The ketone solvents are preferred; with methyl ethyl ketone being the most preferred.

Both sodium hydroxide and potassium hydroxide works equally well in the reaction of the present invention. However, sodium hydroxide is preferred for economic reasons.

To ensure complete formation of the salt, an excess of up to 30% of the sodium or potassium hydroxide is added to the hydroxypyrimidine. The reaction of the subsequently formed salt with TPC is run with up to a ten percent, and preferably five percent, excess of TPC to ensure completed reaction.

The TPC can be reacted with the salt of the hydroxypyrimidine over a period of from thirty minutes to three hours. The actual reaction time is apparently dependent upon the solvent used. Thus, when using methyl ethyl ketone as solvent a reaction of one to one and a quarter hours affords diazinon having a purity greater than 98 percent in a yield of 94 percent. However, when using acetone as solvent a reaction time of two and a half hours is required, giving a product of similar purity but a yield of only 78 percent.

The reaction of TPC with the salt of the hydroxypyrimidine proceeds at a temperature of 55° C. to 80° C. When acetone is used, the reaction is run at the reflux temperature of acetone, namely 56° C. When one of the other aforementioned solvents is used, the reaction is preferably run at a temperature of about 70°-80° C.

The sodium or potassium chloride formed during the reaction may be filtered off and the solvent removed by distillation. However, it is preferred that the sodium or potassium chloride be extracted with water and the lower phase discarded prior to the removal of the solvent by distillation. The remaining impure diazinon is then isolated by working up using standard methods.

While the invention will now be described in connection with certain preferred embodiments in the following examples it will be understood that it is not intended to limit the invention to these particular embodiments. On the contrary it is intended to cover all alternatives, modifications and equivalents as may be included within the scope of the invention as defined by the appended claims.

EXAMPLE 1

Into a three-necked half liter reaction flask fitted with a mechanical stirrer and thermometer were added 70 ml methyl ethyl ketone, 3 g sodium meta bisulfite, 38.3 g hydroxypyrimidine, and 13.5 g of sodium hydroxide pellets. Upon stirring this mixture at room temperature the temperature increased by about 15° C. The mixture was then heated to 55° C. and 51.4 g TPC was added. The temperature was raised by a slight exotherm. The temperature was further raised to 70° C. by heating, kept at this temperature for about 15 minutes, and then heated at reflux (80°-82° C.) for an additional hour. The mixture was then cooled to 60° C., 60 ml water added, the pH raised to 11 by adding aqueous sodium hydroxide, the aqueous phase separated, extracted with additional solvent, and the aqueous phase discarded. The organic phases were combined, the solvent distilled under vacuum, and the diazinon subsequently washed with water, aqueous sodium hydroxide and then aqueous HCl at 50°-60° C., then twice with water, the phases separated, and the traces of water removed under vacuum at 70° C. to afford 70 g of diazinon of purity better than 98% at a yield of 91%, with essentially no traces of the by-products thiotepp.

EXAMPLE 2

Following the method of Example 1, but using recycled, dry methyl ethyl ketone their was obtained essentially the same results.

EXAMPLES 3-6

Following the method of Example 1 but using various solvents, bases, and reaction times similar results were obtained. The conditions and results of the Examples as well as Examples 1-2 are summarized in Table 1.

EXAMPLE 7

A semi-industrial scale involving the use of 112.5 kg methyl ethyl ketone, 6 kg sodium meta bisulfite, 80 kg hydroxypyrimidine, 27 kg solid sodium hydroxide, and 103 kg TPC following the method of Example 1 afforded 147 kg of diazinon of purity better than 98% at a yield of 94%.

TABLE 1

| Example | Solvent | Base | Time of Reaction[a] | Diazinon Obtained Percent Purity | Percent Yield |
| --- | --- | --- | --- | --- | --- |
| 1 | MEK[b] | NaOH | 1.25 | >98 | 91 |
| 2 | MEK(recycled) | NaOH | 1.25 | >98 | 91 |
| 3 | MIBK[c] | NaOH | 1.75 | 98 | 89 |
| 4 | Acetone | NaOH | 2.50 | >98 | 78 |
| 5 | MEK | KOH | 1.25 | >98 | 90 |
| 6 | Dioxane | NaOH | 2.50 | >98 | 87 |
| 7 | MEK | NaOH | 1.25 | >98 | 94 |

[a]TPC plus salt of hydroxypyrimidine (in hours)
[b]Methyl ethyl ketone
[c]Methyl isobutyl ketone

We claim:
1. An improved process for preparing diazinon by reacting the sodium or potassium salt of 2-isopropyl-4-methyl-6-hydroxypyrimidine with diethylthiophosphoryl chloride the improvement which comprises mixing 2-isopropyl-4-methyl-6-hydroxypyrimidine with solid sodium or potassium hydroxide in a ketone or ether solvent at a temperature of about 50°-60° C. until a homogeneous mixture is formed, adding diethylthiophosphoryl chloride to this homogeneous mixture, keeping the mixture at a temperature of 55°-80° C. until the reaction is complete, and separating the diazinon formed.

2. A process in accordance with claim 1 wherein the solvent is selected from the group consisting of acetone, methyl ethyl ketone, methyl isobutyl ketone, and methyl isopropyl ketone.

3. A process in accordance with claim 1 wherein the solvent is methyl ethyl ketone.

4. A process in accordance with claim 1 wherein the solvent is selected from the group consisting of dioxane, tetrahydrofuran, dibutyl ether, diisopropyl ether, dipropyl ether, isopentyl ether, dipentyl ether, butyl vinyl ether, butyl ethyl ether, dimethoxyethane, and bis-(2-methoxy ethyl) ether.

5. A process in accordance with claim 1 wherein the solvent is dioxane.

6. A process in accordance with claim 1 wherein sodium hydroxide is reacted with 2-isopropyl-4-methyl-6-hydroxypyrimidine.

7. A process in accordance with claim 1 wherein the mixture is kept at 55°-80° C. for a period of from 30 minutes to three hours.

8. A process for preparing diazinon by reacting 2-isopropyl-4-methyl-6-hydroxypyrimidine with diethylthio-phosphoryl chloride, the improvement which comprises mixing 2-isopropyl-4-methyl-6-hydroxypyrimidine with solid sodium hydroxide in methyl ethyl ketone until a homogeneous mixture is formed, adding diethylthio-phosphoryl chloride to this homogeneous mixture at a temperature of about 80° C. for about an hour, and separating the diazinon formed.

9. A process according to claim 1 wherein said solid sodium or potassium hydroxide is used in an excess of up to 30% based on the hydroxy pyrimidine.

10. A process according to claim 1 wherein the diethylthiophosphoryl chloride is added in an excess of up to 10% based on salt formed by the reaction of the solid sodium or potassium hydroxide with the 2-isopropyl-4-methyl-6-hydroxyprimidine.

11. An improved process for preparing diazinon by reacting the sodium or potassium salt of 2-isopropyl-4-methyl-6-hydroxyprimidine with diethylthiophosphoryl chloride, the improvement comprising mixing 2-isopropyl-4-methyl-6-hydroxyprimidine with an excess of solid sodium or potassium hydroxide in a ketone or ether solvent in the absence of water until a homogeneous mixture is formed comprising a salt of hydroxypyrimidine, adding an excess of diethylthiophosphoryl chloride to said homogeneous mixture, maintaining the mixture at a temperature of 55°–80° C. to effect reaction and until the reaction is complete, and separating the diazinon formed.

* * * * *